United States Patent [19]
Bruker et al.

[11] Patent Number: 5,234,449
[45] Date of Patent: Aug. 10, 1993

[54] SUTURE CLIP WITH REDUCED HINGE MASS

[75] Inventors: Izi Bruker, Flemington; William J. Zwaskis, Fanwood; Dennis D. Jamiolkowski, Long Valley, all of N.J.

[73] Assignee: Ethicon, Inc., Somerville, N.J.

[21] Appl. No.: 915,155

[22] Filed: Jul. 16, 1992

[51] Int. Cl.⁵ .............................. A61B 17/00
[52] U.S. Cl. .................... 606/158; 606/157; 227/902
[58] Field of Search ............ 227/901, 902; 606/157–158

[56] References Cited

U.S. PATENT DOCUMENTS

| | | | |
|---|---|---|---|
| 3,874,042 | 4/1975 | Eddleman et al. | 606/157 |
| 4,382,453 | 5/1983 | Bujan et al. | 606/157 |
| 4,418,694 | 12/1983 | Beroff et al. | 128/326 |
| 4,446,865 | 5/1984 | Jewusiak | 606/158 |
| 4,449,530 | 5/1984 | Bendel et al. | 606/158 |
| 4,458,682 | 7/1984 | Cerwin | 606/158 |
| 4,476,865 | 10/1984 | Failla et al. | 606/158 |
| 4,579,118 | 4/1986 | Failla | 606/158 |
| 4,834,096 | 5/1989 | Oh et al. | 606/158 |
| 5,062,846 | 11/1991 | Oh et al. | 606/158 |
| 5,062,848 | 11/1991 | Frazee et al. | 606/157 |

FOREIGN PATENT DOCUMENTS 201344 11/1986 European Pat. Off. ............ 606/158

Primary Examiner—Stephen C. Pellegrino
Assistant Examiner—Gary Jackson

[57] ABSTRACT

An improved surgical clip of the type having first and second leg members joined at their proximal ends by a resilient hinge region and terminating at their distal ends in latch means. Each leg member has an outer surface and a clamping inner surface, and the outer surface of each leg member is configured to be accepted by the jaws of the clip applier. The improvement in the clip design specifically relates to a reduction in the mass of the clip in the hinge region. A reduced mass in the hinge region lessens the strain at the hinge region when the clip is in a clamped position, and therefore increases its strength retention.

10 Claims, 4 Drawing Sheets

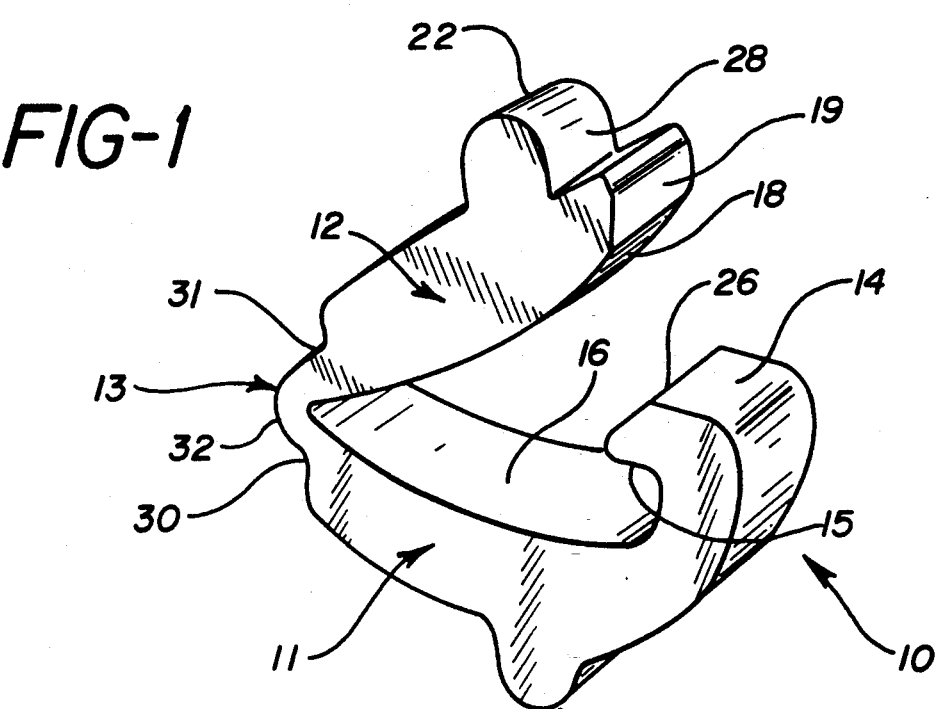
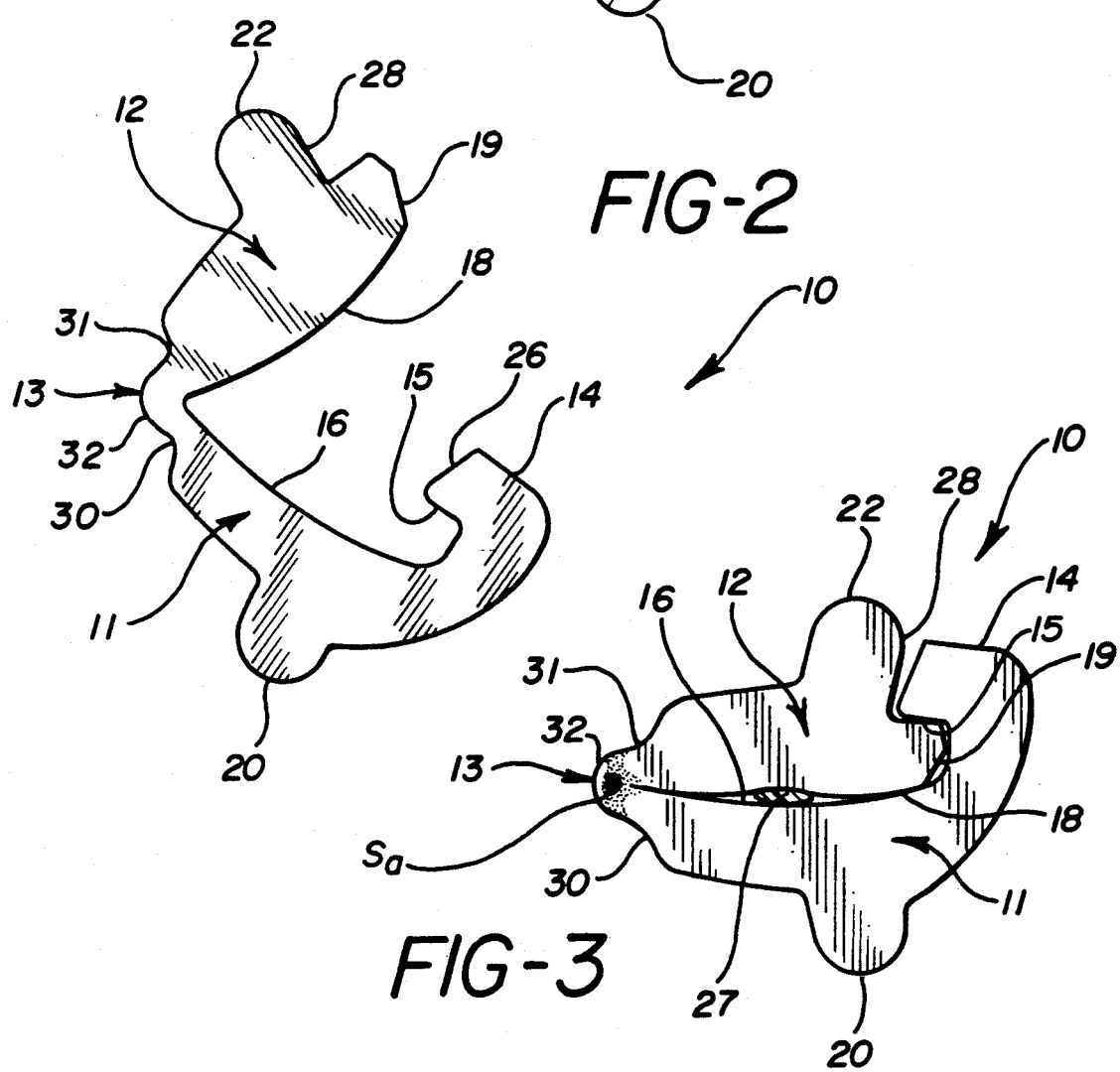

SUTURE CLIP WITH REDUCED HINGE MASS

BACKGROUND OF THE INVENTION

This invention relates generally to a surgical clip. More particularly, it relates to such a clip suitably adapted to replace a suture knot during endoscopic surgery.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing small diameter openings into the desired body cavity as may be required.

An age-old procedure which surgeons are required to perform to repair or reconstruct traumatized bodily tissue is suturing. Fortunately, medical instruments have been recently designed to allow a surgeon to manipulate a suture, or suture and needle combination, through the small diameter opening of a cannula. However, the ability to tie an appropriately placed suture knot endoscopically is troublesome and problematical.

Therefore, in response to this problem, surgeons have sought alternatives to conventional knot-tying techniques which would be suitable during endoscopic surgery. Among these alternatives include the use of hemostatic clips, which are designed to ligate blood vessels and other tubular members, to replace suture knots. Such hemostatic clips are described, for example, in U.S. Pat. Nos. 4,418,694 and 4,476,865. These clips can be readily applied with a clip applier which is designed to function through the small opening of a cannula. Unfortunately, the force required to displace these clips from the suture is inadequately low. As a result, hemostatic clips of the type shown in the art are unsuitable for general endoscopic surgery needs.

In view of the deficiencies of the prior art for creating a useful alternative to tying a suture knot, what is desired within the medical community is a device suitable for application using endoscopic techniques which can successfully replace the suture knot. More specifically, what is needed is a clip particularly adapted for replacing a suture knot during endoscopic surgery, and which exhibits adequate clamping force to function effectively. In those surgical procedures utilizing absorbable sutures it may be preferred to use the device of the present invention in an absorbable embodiment.

SUMMARY OF THE INVENTION

The invention is an improved surgical clip. The clip is of the type comprising first and second leg members joined at their proximal ends by a resilient hinge region and terminating at their distal ends in latch means. Each leg member has an outer surface and a clamping inner surface. The clamping inner surface is disposed in opposition to the clamping inner surface of the other leg member. The outer surface of each leg member is configured to be accepted by the jaws of a clip applier, and the hinge region has an outer hinge surface.

The improvement to the clip relates to the hinge region of the clip. The mass of the clip in the hinge region is reduced relative to that of a conventional clip. The mass is reduced by an amount effective to substantially lessen the strain at the hinge region when the clip is in a clamped position.

Surprisingly, the reduction in mass of the clip at the hinge region actually increases the ability of the hinge region to maintain its structural integrity over an extended period of time when the clip is in a clamped position. Therefore, the ability of the clip to retain its clamping strength, and hence its "survival" rate in vivo, is dramatically improved. These improvements in properties are achieved because the modified design of the hinge region reduces the strain at the hinge region when the clip is in the clamped position.

The clip of this invention is particularly adapted to act as a knot clip in those applications requiring the replacement of a suture knot during endoscopic surgery. Suture knots are required when the suture strand must be anchored or fastened in place. Additionally, the clip can be used for other surgical applications, particularly those applications related to endoscopic surgery. There will be instances when such a clip can be used to advantage in open surgery (i.e., non-endoscopic procedures).

BRIEF DESCRIPTION OF THE DRAWINGS

FIG. 1 is a perspective view of the surgical clip of this invention.

FIG. 2 is a side view of the surgical clip of this invention in an open position.

FIG. 3 is a side view of the surgical clip of this invention in a closed position.

DESCRIPTION OF THE PREFERRED EMBODIMENTS

Figure 4:
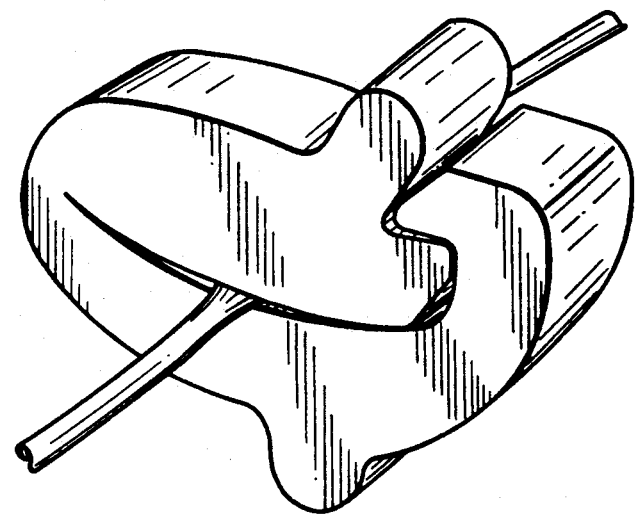
FIG. 4 is a perspective view of the conventional surgical clip of the prior art in a closed position.

Referring to FIGS. 1-3, there is shown a surgical clip 10 of the present invention. The clip has first and second leg members 11 and 12, respectively. The leg members are connected at their proximal ends by a hinge region 13, which is discussed in more detail below. The hinge region according to the present invention is resilient; i.e., it has elastic memory and acts as a spring which assists in the packaging of the clip as well as the handling and placement of the clip.

First leg member 11 of the surgical clip terminates at its distal end in a hook member 14. The hook member has an inner face 15. In a preferred embodiment, the end surface of the hook member is beveled at 26 to assist in deflecting the hook member when the clip is closed.

The clamping inner surface 16 of the first leg member 11 of the clip has a concave radius of curvature extending from the hinge to the start of the hook member. The second leg member 12 has clamping inner surface 18 which has a convex radius of curvature extending from the hinge to the distal end of the leg member. The radius of curvature of the clamping surface 18 is smaller than the radius of curvature of clamping surface 16. Preferably, each leg member has a width substantially identical to the length of its clamping inner surface, which is about 120 mil. Second leg member 12 terminates in an end surface 19. Preferably this end surface is beveled and has a complementary bevel to the bevel on the hook member so as to assist in the deflection of the hook member when the clip is closed.

Disposed on the outer surface of each leg member are bosses 20 and 22. The bosses are used to manipulate the clip in a suitable instrument, for example, an endoscopic clip applier having a jaw formation suitable for securely grasping the clip, as will be briefly described in conjunction with FIG. 6.

The clip is closed about a suture as shown in FIG. 3 by urging the distal ends of the two leg members together with compressive force directed on bosses 20 and 22. When compressive force is applied, end surface 19 of first leg member 12 deflects the hook member 14 after contact with end surface 26 of the hook member as the two leg members are pivoted about the resilient hinge 13 and closed about a suture 27. In this preferred embodiment, cylindrical boss 22 of the second leg member 12 has a contacting face 28 which abuts end surface 26 when the clip is clamped about a suture to ensure adequate and tight closure.

Figure 5:
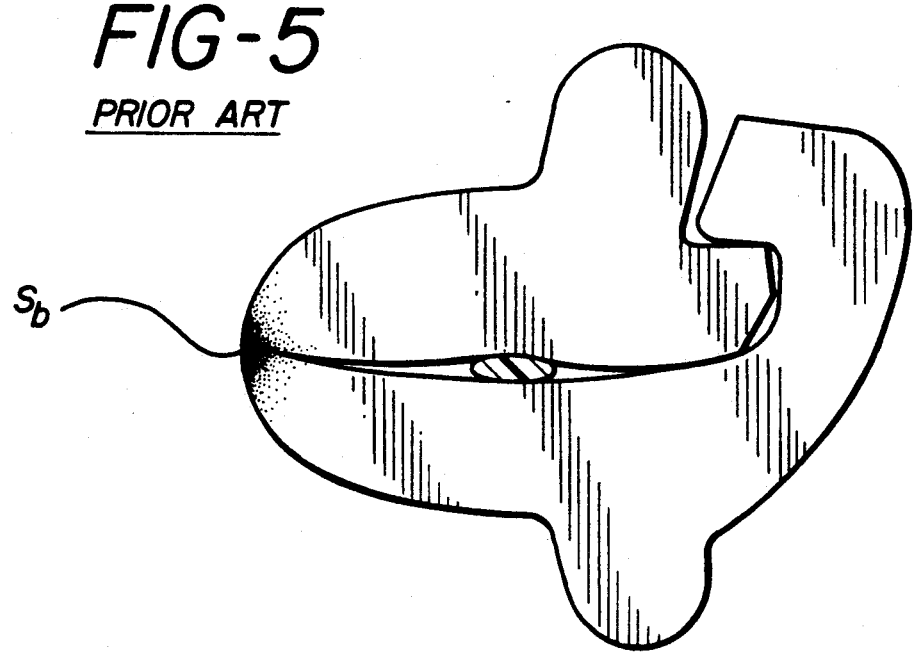
FIG. 5 is a side view of the conventional surgical clip of the prior art in a closed position.

A critical aspect of the clip embodied in FIGS. 1-3 is the reduced mass of the clip in the hinge region 13, as compared with the mass of the hinge region for a conventional prior art clip as shown in FIGS. 4 and 5. For purposes of describing this invention, the "hinge region" of a clip is that region of the clip which physically deforms when the clip is in a clamped position. This physical deformation occurs because the material from which the clip is composed stretches in the region of the hinge. As the degree of deformation increases, the strain on the clip increases as well. Since the deformation occurs at the hinge region, the hinge region experiences most of the strain placed on the clip when it is clamped, and therefore the failure rate of the clip depends significantly on the degree of strain associated with the hinge design.

Surprisingly, a reduction in the mass of the hinge region as shown in FIGS. 1-3, relative to the mass in this region for prior art clips as embodied in FIGS. 4 and 5, actually lessens the strain at the hinge region, and therefore reduces the failure rate of the clip when in a clamped position. As shown in FIGS. 4 and 5, a conventional clip has a hinge region defined by an outer hinge surface which has a substantially constant radius of curvature. Advantageously, the mass in the hinge region of the clips of this invention is reduced relative to the mass in the hinge region of a conventional clip by an amount greater than about 10 percent, preferably greater than about 15 percent.

The outer surface of the hinge region of the clip embodied in FIGS. 1-3 is configured to form a "corrugated" hinge, and has first and second curved valley regions 30 and 31, respectively. The curved valley regions are spaced between a curved plateau region 32. The radii of curvature for each of the regions is substantially equal. The cross-sectional area of this corrugated hinge in the most preferred embodiment of this invention is about 17 percent less than the cross-section of a regular, rounded hinge of a conventional clip (for this embodiment, the cross-sectional area would be directly proportional to its mass in the hinge region because the thickness of the clip in the hinge region remains substantially constant, and therefore the reduction in mass in the hinge region would also be about 17 percent).

The hinge region design shown in FIG. 3, when the clip is composed of a bioabsorbable polymer such as poly(paradioxanone), exhibits a percent of strain when the clip is in a clamped position at the hinge region of about 34 percent, as measured using standard finite element analysis techniques. The strain is distributed away from the proximal tip of the hinge region, and is depicted as $S_a$ in FIG. 3. In contrast, the percent of strain at the hinge region of a conventional clip made of the same bioabsorbable polymer is about 56 percent, and is distributed adjacent the proximal tip of the hinge region. This distribution is shown as $S_b$ in FIG. 5.

Figure 7:
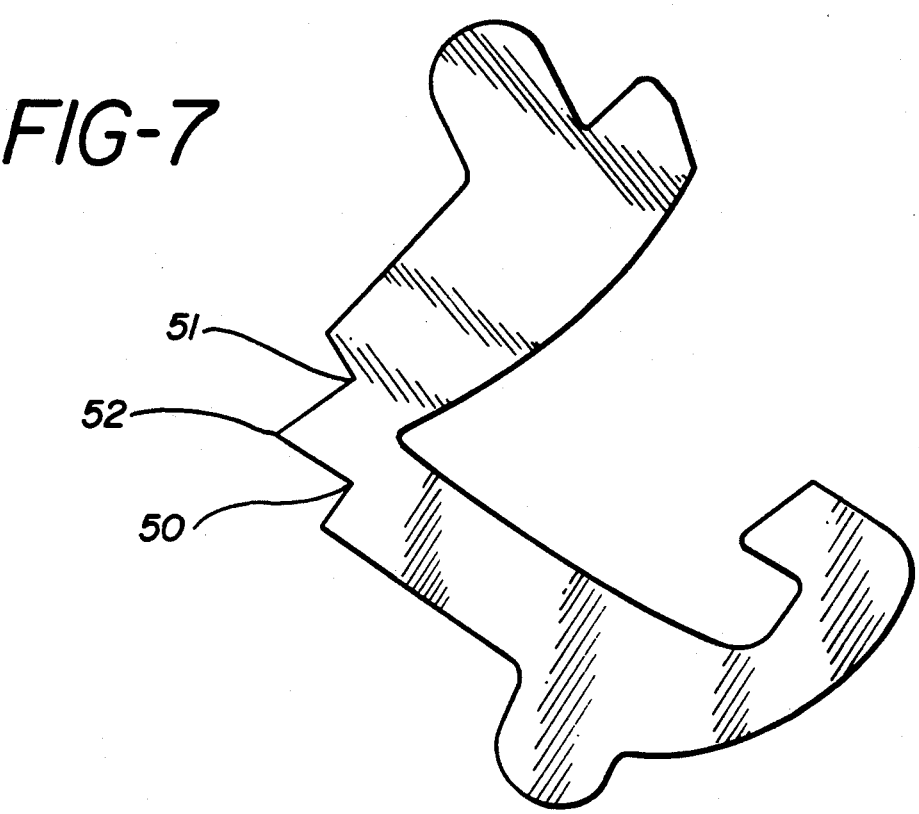
FIG. 7 is a side view of another embodiment of the surgical clip of this invention.
Figure 8:
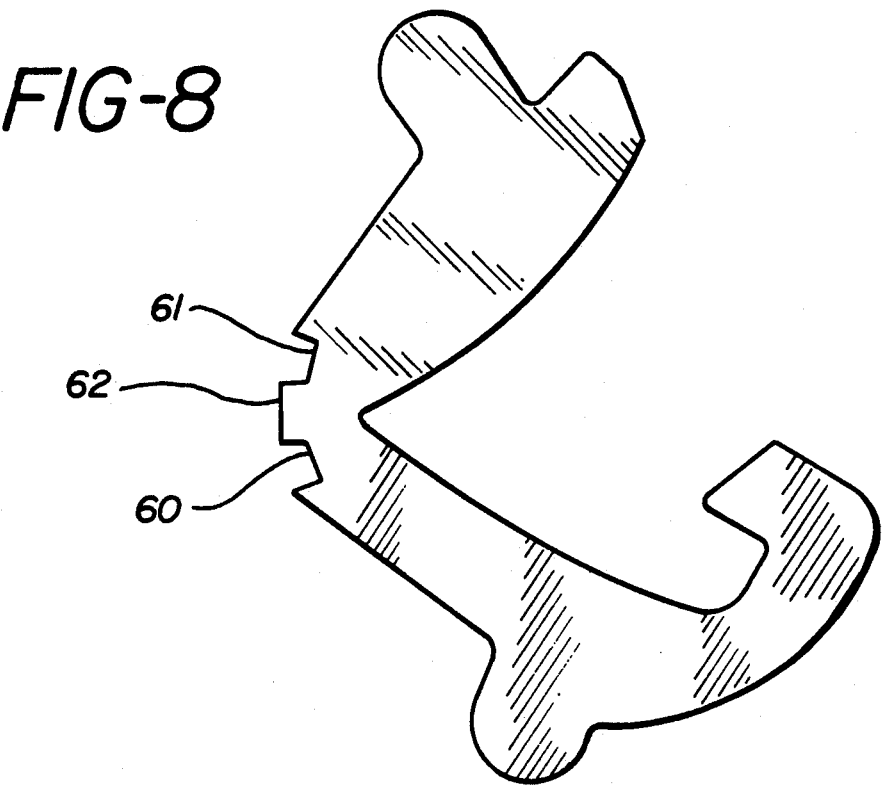
FIG. 8 is a side view of yet another embodiment of the surgical clip of this invention.

In another embodiment shown in FIG. 7, reduced strain in the hinge region can be achieved by configuring the outer surface of the hinge region with first and second triangular valley regions 50 and 51, respectively, spaced between a triangular plateau region 52. In yet another embodiment to reduce the hinge strain relative to that of a conventional clip having a rounded outer surface at the hinge region, FIG. 8 shows a hinge region with first and second rectangular valley regions 60 and 61, respectively, spaced between rectangular valley region 62.

Figure 6:
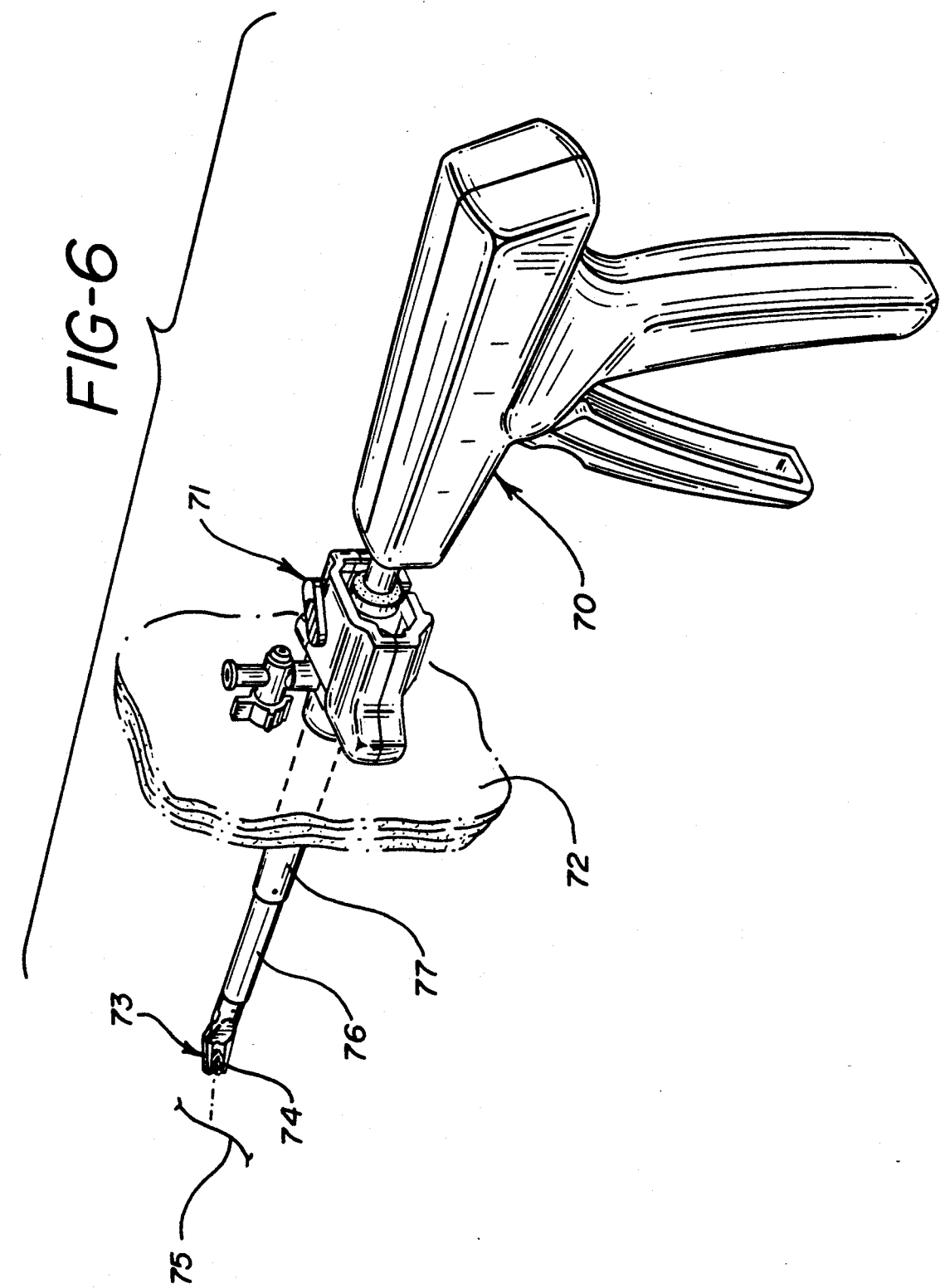
FIG. 6 is a perspective view of a conventional clip applier for applying the surgical clip.

The clips within the scope of the present invention are suitably adapted for endoscopic applications to replace a conventional suture knot. This can be accomplished as illustrated in FIG. 6. Referring now to FIG. 6, there is shown a clip applier 70 having a long, small-diameter longitudinal member 76. Longitudinal member 76 is adapted to be inserted into a conventional trocar 71 through trocar cannula 77. The trocar is used to provide an opening through bodily tissue 72 for access to the surgical site. The clip applier 70 has jaws 73 at its distal end which are configured in such a manner as to facilitate grasping the outer surface of the legs of the clip 74. Clip applier 70 is maneuvered within the surgical site to place clip 74 about suture 75 which is to be clamped.

The clips of the invention can be made of any biocompatible material using conventional fabrication methods. The clips can be composed of various biocompatible metals, e.g. titanium and tantalum, and polymeric materials. Preferably, the clips are made of bioabsorbable polymeric materials such as homopolymers and copolymers of glycolide, lactide and para-dioxanone. The most preferred polymer from which the clip is made is polydioxanone.

The preferred means for fabricating clips from bioabsorbable polymeric materials is to inject a suitable polymer melt into an appropriately designed mold at process conditions conventionally employed for such polymer systems. After the polymer melt cools, the molded polymer shaped in the mold to meet the design criteria of the clip can be readily released from the mold. Ideally, the molded clip is then scoured and annealed to optimize the crystallinity of the polymer from which the clip is derived, and therefore its dimensional stability at elevated temperatures, as well as its in vivo mechanical performance. The annealing conditions can be readily determined empirically. After annealing, the clip can be sterilized using conventional methods to render the clip suitable for surgical applications. Alternatively, numerous clips can be fabricated simultaneously by first extruding a polymer melt to form an elongate rod which is appropriately configured to conform to the desired cross-sectional shape of the clip, and then slicing the rod into individual clips with the desired clip thickness.

In an especially preferred embodiment for clips made by molding the clips from a polymer melt, a post-molding technique is used to further improve the performance of the clip. Specifically, the clips are "flexed" at the hinge region over a suitably sized mandrel to significantly increase the survival rate of the clip when the clip is clamped about a suture. The flexing operation at the hinge region of the clip causes the leg members of the clip to approach one another. In the preferred embodiment, the bevel surface 26, of the hook member of the first leg nearly touches the bevel surface 19, of the second leg. Advantageously, the leg members are not closed so much so as to activate the latching mechanism. The number of flexes may change the performance; we have found five flexes to give improved performance. For reasons possibly related to polymer morphology, flexing causes a reduction in the failure rate of the clip at the hinge region.

The post-mold flexing of the hinge region of the clip to improve its performance can be performed directly out of the mold, or within a relatively short time period thereafter, e.g. about 24 hours. In any event, flexing should generally be carried out prior to the annealing step. The diameter of the mandrel over which the clip is flexed will depend on the specific shape and dimensions of the clip, as well as the maximum diameter of the suture to be clamped between the legs of the clip. The mandrel diameter can be readily determined empirically to achieve optimum results.

The description of these preferred embodiments should not be construed in any way to limit the scope of the claimed invention. Numerous additional embodiments within the scope and spirit of the invention will become readily apparent to those skilled in the art upon careful review of this specification and the following Example.

EXAMPLES

Example 1

Suture Clip Preparation

Suture clips configured substantially as shown in FIGS. 1-3 having reduced mass in the hinge region are made by injection molding pellets of polydioxanone polymer. The molding conditions are the following:

| | |
|---|---|
| Melt temperature | 103-120° C. |
| Mold temperature | 30-55° C. |
| Injection speed | 1.0-1.8 inches/sec. |
| Injection pressure | 500-950 psi |
| Cooling time | 50-90 sec. |

Scouring

The clips are removed from the mold and put into a screened tray which is then submerged into propanol. The propanol is in a circulating bath which is turned on for 30 minutes once the clips are put into the bath. At the end of 30 minutes the clips are left out for one hour to air dry. After air drying the clips are transferred to the annealing oven.

Annealing

The annealing cycle consists of a one hour nitrogen purge cycle at ambient temperature. At the end of the nitrogen purge cycle the oven switches into a heat cycle of 83° C. for 10.5 hours. Once the cycle is completed, the oven is cooled down to below 50° C. before the clips are removed. Once the clips are removed they are placed in a nitrogen chamber for storage.

Clamping of Clip to Suture

The suture clips are applied to strands of United States Pharmaecopia (USP) size 2/0 or 3/0 VICRYL ® poly(lactide-co-glycolide) braided suture using a standard clip applier.

Invivo Testing

The clamped suture strands are implanted subcutaneously in the posterior dorsal subcutis of female Long-Evans rats weighing 250 to 300 grams. The strands remain implanted for either ten or fourteen days, and then the clamped strands are explanted to determine percent clip survival as described below.

Determination of Percent Clip Survival

The suture clips of the explanted strands from the invivo testing are analyzed for "survival". A clip is considered to have survived if the latch is completely closed over the suture strand and the hinge is not completely broken visually. Clips with partial hinge cracks are considered to have survived. Clips which have slipped off the suture strand are considered to have failed. The results are shown in Table 1.

Comparison with Conventional Clip

Suture clips with a conventional hinge region but in all remaining aspects substantially identical to the suture clips tested above are molded, processed and tested for percent clip survival in accordance with the procedures described above. The results are shown in Table 1.

TABLE 1

| | PERCENT CLIP SURVIVAL | | | |
|---|---|---|---|---|
| | Size 2/0 | | Size 3/0 | |
| | 10 days | 14 days | 10 days | 14 days |
| Improved Clips[1], Percent Survival | 100 | 100 | 100 | 100 |
| Conventional Clips[2], Percent Survival | 30 | 0 | 40 | 0 |

[1]The number of improved clips tested is 10 for each suture size and time in vivo.
[2]The number of conventional clips tested is 10 for each suture size and time in vivo.

The results shown in Table 1 demonstrate the significantly improved survival rate for the improved clips of this invention with reduced mass in the hinge region in comparison with the survival rate of conventional clips. The reduced mass lessens the strain at the hinge region when the improved clips are clamped about the suture strands, so that when the clamped clips are explanted after 10 or 14 days, the structural integrity of the clip, particularly at the hinge region, remains substantially intact. Conversely, the conventional clips lose their integrity over time when clamped about the suture strands because the clips typically fail at the hinge region where the strain is significant.

EXAMPLE 2

Suture clips configured substantially as shown in FIGS. 1–3 are made by injection molding pellets of polydioxanone in the manner described in Example 1 except that the clips are flexed 5 times at the hinge region either directly after the molding step or 24 hours after molding, as indicated, but before the annealing step.

For each experiment, 25 clips are clamped over a size 2/0 polydioxanone suture, and placed in a buffered solution at 8.5 pH held in a 37° C. temperature controlled bath. In vitro performance is judged by observing the number of clips which remain affixed to the suture (percent survival) at 24 and 48 hours. The performance results are compared with clips which are not flexed at the hinge, and the overall results are shown in Table 2.

TABLE 2
PERCENT SURVIVAL FOR HINGE-FLEXED CLIPS

| Conditions | 24 Hour Survival | Type of Failure | 48 Hour Survival | Type of Failure |
|---|---|---|---|---|
| No Flexing | 76% | hinge | 72% | hinge |
| Flexing: no mandrel flexed directly after molding | 68 | hinge | 42 | hinge |
| Flexing: no mandrel flexed 24 hours after molding | 76 | hinge | 48 | hinge |
| Flexing: 22 mil mandrel flexed directly after molding | 96 | hinge | 88 | hinge |
| Flexing: 22 mil mandrel flexed 24 hours after molding | 100 |  | 84 | hinge |
| Flexing: 33 mil mandrel flexed directly after molding | 92 | latch | 84 | hinge |
| Flexing: 33 mil mandrel flexed 24 hours after molding | 88 | latch | 80 | hinge |

NOTES:
Each hinge flexed 5 times
25 clips used per experiment
In vitro conditions: 37° C., 8.5 pH The results shown in Table 2 demonstrate that clips flexed over an appropriately-sized mandrel at the hinge region exhibit improved survival relative to the survival shown for clips which are not flexed or are not flexed over a mandrel.

What is claimed is:

1. An improved surgical clip of the type having first and second leg members joined at their proximal ends by a resilient hinge region and terminating at their distal ends in latch means, each leg member having an outer leg surface and a clamping inner surface, said clamping inner surface being in opposition to the clamping inner surface of the other leg member, the outer leg surface of each leg member being configured to be accepted by the jaws of a clip applier, and said resilient hinge region having an outer hinge surface;

the improvement wherein the outer hinge surface of said hinge region has first and second curved valley regions, said curved valley regions spaced between a curved plateau region, and each of said curved valley regions and said curved plateau region has substantially identical radii of curvature.

2. The clip of claim 1 wherein said first leg member terminates at its distal end thereof with a deflectable hook member.

3. The clip of claim 2 wherein the clamping inner surface of said first leg member has a concave radius of curvature between the hinge region and the hook member, and the clamping inner surface of said second leg member has a convex radius of curvature between the hinge region and its distal end, the radius of curvature of the clamping inner surface of said second leg member being smaller than the radius of curvature of the clamping inner surface of said first leg member.

4. The clip of claim 3 wherein the outer leg surface of each leg member includes a boss to facilitate engagement of said clip by the jaws of a clip applier.

5. The clip of claim 4 wherein each leg member has a width which is substantially identical to the length of the clamping inner surface of said leg member.

6. The clip of claim 5 wherein said width is about 120 mil.

7. An improved surgical clip of the type having first and second leg members joined at their proximal ends by a resilient hinge region and terminating at their distal ends in latch means, each leg member having an outer leg surface and a clamping inner surface, said clamping inner surface being in opposition to the clamping inner surface of the other leg member, the outer leg surface of each leg member being configured to be accepted by the jaws of a clip applier, and said resilient hinge region having an outer hinge surface;

the improvement wherein the outer hinge surface of said hinge region has first and second rectangular valley regions, said rectangular valley regions spaced between a rectangular plateau region.

8. An improved surgical clip of the type having first and second leg members joined at their proximal ends by a resilient hinge region and terminating at their distal ends in latch means, each leg member having an outer leg surface and a clamping inner surface, said clamping inner surface being in opposition to the clamping inner surface of the other leg member, the outer leg surface of each leg member being configured to be accepted by the jaws of a clip applier, and said resilient hinge region having an outer hinge surface;

the improvement wherein the outer hinge surface of said hinge region has first and second triangular valley regions, said triangular valley regions spaced between a triangular plateau region.

9. The clip of claim 1, 8 or 7 wherein said clip is made by injection molding a polymer melt into a mold for the clip, and said molded clip is flexed over a mandrel at the hinge region after said molding step.

10. The clip of claim 9 wherein said clip is annealed after said flexing step.

* * * * *